(12) United States Patent
Lin et al.

(10) Patent No.: US 6,691,558 B1
(45) Date of Patent: Feb. 17, 2004

(54) IN-LINE RHEOMETER DEVICE AND METHOD

(75) Inventors: Ye-Gang Lin, Evansville, IN (US); Vikram Gopal, Mount Vernon, IN (US); Ronald Dale Craddock, McLeansboro, IL (US); Michael Shoen Davis, Mount Vernon, IN (US)

(73) Assignee: General Electric Company, Pittsfield, MA (US)

( * ) Notice: Subject to any disclaimer, the term of this patent is extended or adjusted under 35 U.S.C. 154(b) by 0 days.

(21) Appl. No.: 10/208,294

(22) Filed: Jul. 31, 2002

(51) Int. Cl.$^7$ .................. G01N 11/00; A23G 1/22; C08F 20/00
(52) U.S. Cl. .................. 73/54.01; 525/450; 425/115
(58) Field of Search .................. 73/54.01, 54.11, 73/54.14; 525/450, 354; 425/115

(56) References Cited

U.S. PATENT DOCUMENTS

| | | |
|---|---|---|
| 4,403,502 A | 9/1983 | Lindt |
| 4,433,116 A | 2/1984 | Largman et al. ............ 525/420 |
| 4,449,395 A | 5/1984 | Kurtz et al. |
| 4,817,416 A | 4/1989 | Blanch et al. |
| 5,357,784 A | 10/1994 | Collier ...................... 73/54.14 |
| 5,594,074 A | 1/1997 | Hwo et al. .................. 525/387 |
| 5,594,095 A | 1/1997 | Gruber et al. .............. 528/354 |
| 5,798,435 A | 8/1998 | Gruber et al. .............. 528/354 |
| 5,974,866 A | 11/1999 | Tjahjadi et al. |
| 5,998,552 A | 12/1999 | Gruber et al. .............. 525/450 |
| 6,291,597 B1 | 9/2001 | Gruber et al. .............. 525/450 |
| 6,405,579 B1 | 6/2002 | Tjahjadi et al. ............ 73/54.11 |

Primary Examiner—Hezron Williams
Assistant Examiner—J L Politzer

(57) ABSTRACT

A system and method for measuring viscosity, melt flow index (MFI), and melt volume rate (MVR) of a polymer melt in real-time during an extrusion process to provide quick and accurate feedback for process control. The system includes a polymer processing rate sensor (36), a polymer melt temperature sensor (30), an extruder pressure sensor (32), and a die head temperature sensor (34) for taking in-line measurements during the extrusion process. The in-line measurements are made on the main process stream of the polymer melt, with the determination of viscosity, MFI, and MVR based on these measured values and those obtained during a calibration run with polymers having known properties. The invention can be used in any polymer compounding and extrusion process utilizing die opening with any constant geometry for monitoring quality and providing feedback for process control.

20 Claims, 1 Drawing Sheet

IN-LINE RHEOMETER DEVICE AND METHOD

BACKGROUND OF THE INVENTION

The present invention relates to a rheological measurement method and apparatus. More particular, the present invention relates to a method and apparatus for the in-line measuring of the characteristics of a molten material such as viscosity, melt volume rate and melt flow index during an extrusion process.

Rheological testing equipment and methods have become invaluable in recent years in improving the process control of the manufacture of plastic products from polymer melts. Such equipment allows for the determination of rheological properties of the melts such as melt flow index (MFI), melt volume rate (MVR) and viscosity. This, in turn, has allowed manufacturers to exert control over the plastics manufacturing process and produce consistent, high quality products by allowing them to make adjustments to the manufacturing process parameters.

Early rheological testing equipment was primarily used in conducting laboratory measurements of these characteristics of polymer melts. Based on the results of these tests, adjustments were then made in the manufacturing process in an attempt to fine-tune the process. While helpful, such tests are limited in that they cannot provide "real-time" results during the manufacturing process, allowing for near instant and constant adjustments to be made to the process in order to optimize the quality and consistency of the resulting products.

In response to this shortcoming, more recent efforts have been directed toward measurement of these properties on-line or in-line during the manufacturing process, thereby providing quicker and continuous feedback to a process controller and allowing closer control over the quality of the polymer melt. One such type of on-line system includes a rheometer that diverts a portion of the plastic melt from the main stream of molten plastic, conducts rheological measurements on the diverted melt, and then purges the melt to the atmosphere or external repository. Such on-line rheometers are contrasted with in-line rheometers, which return the diverted melt portion to the main melt stream after testing. In-line rheometers eliminate the waste generated by the discharge of the plastic melt after measuring in on-line systems.

In both types of rheometers, a metering pump is typically used to feed a capillary passage with a controlled amount of the diverted melt. The pressure drop along the capillary passage is measured and the temperature of the diverted melt is closely controlled with an independent heating or cooling system in order to determine MFI and/or MVR. More recently, on-line rheometers without a metering pump have been developed in which the diverted melt is pushed through a temperature controlled capillary passage under the pressure difference between the main stream and atmospheric pressure. For this type of on-line rheometer without a metering pump, MFI and MVR can be determined by measuring pressure drop and discharge rate along the capillary passage.

Nevertheless, a need exists for an in-line rheological measuring system that is simple, easy to install, operate and maintain, and can instantly and easily measure MFI and MVR on the entire melt stream in real time during a plastic extrusion process to provide quick and accurate quality control data and feedback information to process control. In addition, it would be helpful to be able to determine process control information as temperature, shear stress and shear rate continuously vary, overcoming the deficiencies of prior extrusion rheometer systems that required that temperature and shear rate be fixed. The in-line measured MFI and MVR should match quality assurance laboratory results, with the difference between the in-line and laboratory measurements falling below the standard deviation of the laboratory measurement itself.

SUMMARY OF THE INVENTION

A system for conducting in-line rheological measurements on a process melt for providing process control information includes a vessel or die containing a polymer melt under pressure, the vessel or die having a head portion through which the polymer melt may flow, a feeding system for providing a polymer to the vessel or die, a polymer melt temperature sensor, a processing rate sensor, a vessel or die pressure sensor, a vessel head or die head temperature sensor, and a controller responsive to signals provided by the sensors for determining process characteristics of the polymer melt.

A system for providing process control information concerning a polymer melt in an extrusion process comprises a processing rate sensor for monitoring a rate at which the polymer resin is added to the extrusion process, a polymer melt temperature sensor for monitoring the temperature of the polymer melt prior to its extrusion, an extrusion die pressure sensor for monitoring the pressure inside the extruder, a die head temperature sensor for monitoring the temperature of the die head, and a controller responsive to signals generated by said sensors.

A method for providing process control information regarding a polymer melt in an extrusion process includes the steps of adding a polymer resin to an extruder, heating the polymer resin to form a molten polymer melt, elevating an internal pressure of the extruder to a pressure greater than atmospheric pressure, discharging the polymer melt through one or more die opening of any constant geometry defined in a die head coupled to the extruder, measuring the rate at which the polymer resin is added to the extruder, measuring the temperature of the polymer melt just prior to its being discharged, measuring the temperature of the die head, measuring the internal die pressure of the extruder, and conveying the measurements to a controller.

DETAILED DESCRIPTION OF THE INVENTION

Figure 1:
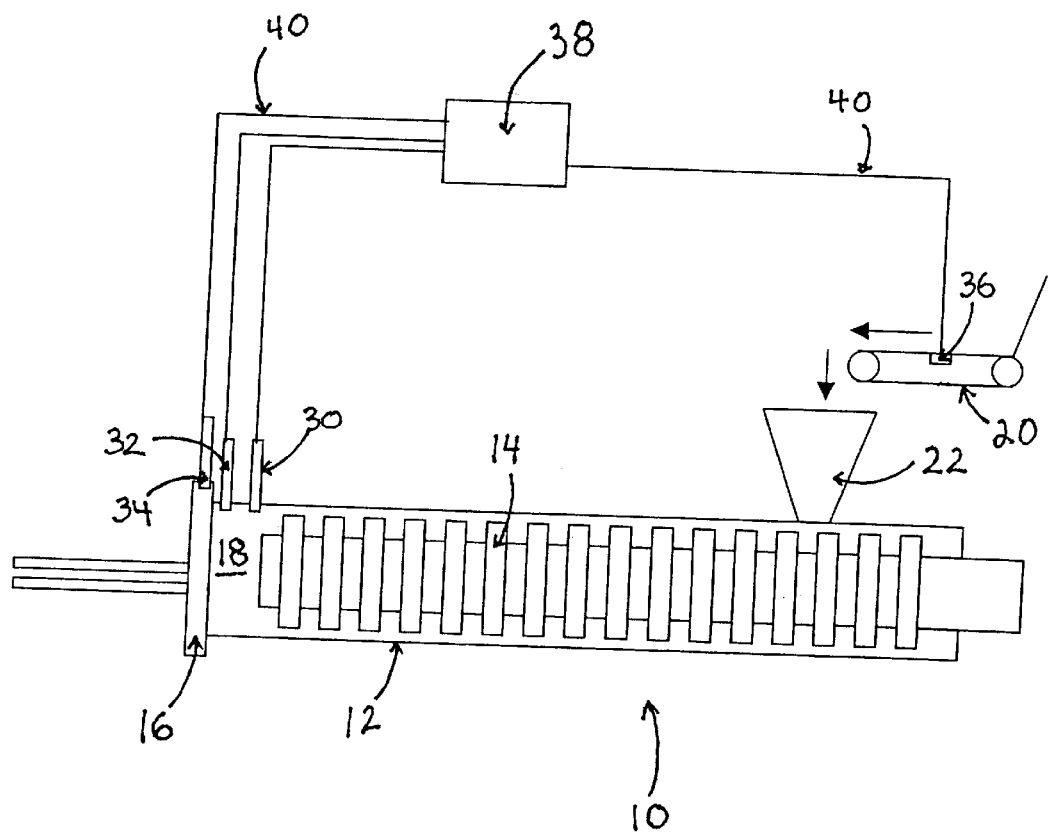
FIG. 1 is a schematic diagram of an in-line rheometer system according to one embodiment of the present invention for providing process control information for a polymer melt.

With reference to FIG. 1, a polymer extrusion system 10 is shown incorporating an in-line rheometer system according to one embodiment of the present invention. The polymer extrusion system 10 can be any proprietary or commercially available extruder and generally comprises a vessel or extruder 12, at least one rotatable screw 14 mounted inside the extruder and extending at least partially therethrough, and a vessel or die head 16 selectively attached to an end of the extruder, the die head defining one or more orifices (not shown), through which a polymer melt may be extruded or discharged. Preferably, the screw 14 is inserted into the extruder 12 at an end distal from the die head 16 and extends coaxially within the extruder to a point short of the die head 16 leaving a space 18 between an end of the screw 14 and the die head. A conveyor or other continuous feeding system 20 is used to direct the polymer raw materials into the extruder through a hopper 22.

The in-line rheometer system includes a polymer melt temperature sensor 30, a die pressure sensor 32, a die head temperature sensor 34, a processing rate sensor 36, and a controller, data processor or computer 38. The processing rate sensor 36 measures the rate at which polymer resin is extruded. In an extrusion process, this rate can typically be easily determined by measuring the feed rate at which polymer resin is added to the extruder and thus the processing rate sensor 36 takes the form of a feed rate sensor, as shown in FIG. 1. Nevertheless, since the mass throughput through an extruder at any particular time will typically remain constant during an extrusion process (i.e. imput= output), the processing rate sensor 36 can also take the form of a discharge rate sensor that measures the polymer output down stream of the die head. Each sensor produces a resultant signal that is advanced to the controller 38 for determining the process characteristics of the polymer melt. The various signals from the sensors may be advanced to the controller 38 using known technology, such as through lead wires 40 or wireless technology.

The polymer melt temperature sensor 30 may be mounted on and extend through the wall of the extruder 12 such that it is in contact with the molten polymer process melt stream in the die space 18. Similarly, the die pressure sensor 32 also extends into the die of the extruder and is in contact with the process melt stream in order to get an accurate measurement of the pressure P of the melt stream in the die head area. In addition, the polymer melt temperature sensor 30 and the pressure sensor 32 are preferably inserted into the extruder such that their tips are located in the space extending between the end of the screw 14 and the die head 16. The die head temperature sensor 34 is mounted on the die head and produces a resultant signal that is advanced to the controller 38. Both the polymer melt temperature sensor 30 and the die head temperature sensor 34 may be commercially available thermocouples or other sensors capable of accurately measuring the temperatures of a polymer melt and of an extrusion die head, respectively, and suitable for use in such environments.

Any conventional die and screw design may be used in conjunction with the rheometer system of the present invention. Thus, extruders having both a single screw and a twin screw design may be used, as well as other types of polymer compounding mixers. Likewise, the rheological properties of various filled and unfilled polymeric resins may be determined using the system of the present invention. These include not only various thermoplastics, but also thermoplastic elastomers, thermoplastic vulcanizates, and thermosets.

In an exemplary process according to the present invention, a polymer resin as well as any fillers to be included in the final product are added at a controlled rate to the hopper 22 feeding the extruder 12. The processing rate sensor 36 measures or monitors the mass of the polymer resin as it passes into the extruder and transmits the information to the controller 38. In the extruder, the resin is heated to a molten state (known as a polymer melt) and mixed, typically using one or more rotating screws 14. The extruder is typically heated using a commercially available heater (not shown). A separate heater may be used to heat the die head 16 to maintain the temperature suitable for processing. The polymer melt is pressurized to greater than atmospheric pressure in the die 12 by the rotating screw 14. The polymer melt temperature sensor 30 measures the temperature of the melt as it passes through the die head 16 and transmits the information to the controller 38. Likewise, the die pressure sensor 32 measures the pressure inside the die head 16 and transmits the information to the controller 38.

As stated previously, both the polymer melt temperature sensor 30 and the die pressure sensor 32 are preferably placed in contact with the main melt stream of the polymer melt in the section 18 of the die between the die head and the screw, close to or immediately adjacent the die head 16, i.e. near enough to the die head so that measurements will be substantially unaffected by the fluctuations caused by the rotating screw or newly introduced resin at the hopper. This typically allows for the most accurate measurements of the polymer melt temperature and the die pressure immediately before the melt is extruded through the orifices of the die head. The pressure difference between atmosphere and the interior of the die causes the polymer melt to be extruded as strands through one or more orifices of known geometry in the die head 16. The strands are cooled and then chopped into pellets or further processed. The die head temperature sensor 34 is attached to the die head 16 to record its temperature and transmit the information to the controller 38. The controller 38 collects the data and continuously calculates the viscosity, MFI and MVR of the polymer melt in the die via the calculations detailed below, using the information from the sensors and information collected from prior calibration runs on the die. The results are analyzed by process control and any necessary adjustments to the process can continuously be made.

With a constant mass throughput through the extruder, the processing rate sensor thus measures the mass flow rate W through the extruder die head orifices. For a given polymer, mass flow rate W can be converted to volume flow rate Q using the known melt density $\rho$, for the specific polymer $$Q = W/\rho \tag{1}$$

According to rheology fundamentals, viscosity $\eta$ of a polymer melt can be determined by:

$$\eta = A\Delta P/Q \tag{2}$$

or $$\eta = A\rho\Delta P/W \tag{3}$$

where A is a constant determined by flow passage geometry. In the current case, the flow passage corresponding to pressure difference $\Delta P$ is the die opening of any constant geometry. Since the melt stream is discharged from the die head into the atmosphere, P is equivalent to the pressure difference $\Delta P$ that drives the melt stream out of the die head orifices. Although the geometry of the die opening is not as simple as the capillary orifices used in many commercial rheometers, it can be determined with known $\eta$, $\rho$, $\Delta P$, and W.

For polymer melts, the viscosity is temperature dependent. The actual temperature of a melt stream in the extrusion process has a certain range of fluctuations. In addition, the actual process melt temperature can be different from the testing temperature in quality assurance laboratory measurements. In order to match quality assurance measurements, a melt temperature correction factor $X(T_{melt})$ is adopted:

$$X(T_{melt}) = B \exp(C/T_{melt}) \tag{4}$$

Where B and C are constants, and $T_{melt}$ is the absolute temperature of the process melt stream.

The viscosity measurement can also be affected by the temperature of the die head plate. Therefore, a die temperature correction factor $X(T_{die})$ is used defined by:

$$X(T_{die})=D\ \exp(E/T_{die}) \quad (5)$$

Where D and E are constants and $T_{die}$ is the temperature of the die head.

Since most polymer melts are non-newtonian fluids under extrusion process conditions, the measured viscosity will vary with shear stress. For a given geometry of a flow passage (a die head opening), the shear stress will be directly proportional to $\Delta P$. In order to correct for this, a pressure correction factor $X(P)$ is used:

$$X(P)=E\Delta P^n \quad (6)$$

where E and n are constants.

Combining equations 3, 4, 5 and 6 gives the quality assurance viscosity in terms of in-line measurements:

$$\eta(QA)=X(T_{melt})X(T_{die})X(P)A\rho\Delta P/W \quad (7a)$$

or $$\eta(QA)=ABDF\ \rho\ \exp(C/T_{melt}+E/T_{die})\Delta P^{(1+n)}/W \quad (7b)$$

To simplify equation 7b, the constants A, B, D, F and $\rho$ can be combined into a single constant x(all). To reduce the modeling error, a constant (const.) is then added to cover effects from all other factors to arrive at:

$$\eta(QA)=x(\text{all})\exp(C/T_{melt}+E/T_{die})\Delta P^{(1+n)}/W+\text{const.} \quad (8)$$

With equation 8, the in-line measurements, $T_{melt}$, $T_{die}$, P(equivalent to $\Delta P$) and W can be converted to viscosity, which is equivalent to quality assurance test results. The constants in equation 8, x(all), C, E, n and const. can be determined by extrusion line calibration with a specific polymer having a known viscosity.

MFI and MVR are both inversely proportional to viscosity, with the relationships between in-line and quality assurance laboratory measurements given by the equations:

$$MVR(QA)=a\ \exp(-C/T_{melt}-E/T_{die})W/\Delta P^{(1+n)}+b \quad (9)$$

$$MFI(QA)=\rho\ a\ \exp(-C/T_{melt}-E/T_{die})W/\Delta P^{(1+n)}+b \quad (10)$$

The constants in equations 9 and 10 (i.e. a, C, E, n, and b) can likewise be determined by extrusion line calibration with polymers having known viscosity, MFI or MVR. In some manufacturing lines, the die temperature is set to a constant and the measured die temperature exhibits minimum variation. In such a case, equations 8, 9 and 10 can be further simplified as:

$$\eta(QA)=x(\text{all})\exp(C/T_{melt})\Delta P^{(1+n)}/W+\text{const.} \quad (11)$$

$$MVR(QA)=a\ \exp(-C/T_{melt})W/\Delta P^{(1+n)}+b \quad (12)$$

$$MFI(QA)=\rho\ a\ \exp(-C/T_{melt})W/P^{(1+n)}+b \quad (13)$$

By continuously obtaining signals from the various sensors, the controller can instantly and continuously calculate these rheological values for a polymer melt as it passes through the extrusion system. Corrections and modifications can be quickly made by process control in response to fluctuations in these values. As used herein, the words "instantly", "instantaneous" and the like should be understood to encompass "substantially instantaneous", with the inventors realizing that a slight delay (typically measured in fractions of a second) will be encountered due to limitations of computing speed and sensor measurement transmission speed. The controller may be set to calculate the rheological values at defined intervals, such as every 5 seconds, for example. Thus, MFI and MVR can be measured in real-time during an extrusion process to provide accurate and instantaneous feed back for process control, thus allowing precise control over the extrusion process and the resultant product.

The method has the advantages of being simple, as well as easy to install, operate and maintain. In contrast to laboratory and other commercially available rheometers, which require that certain variables be held constant (temperature, shear stress and/or shear rate), melt viscosity of a polymer melt can be measured in the present invention without fixing any of the variables. That is, MVR, MFI and viscosity may continuously be determined even while all of the variable are constantly changing during the extrusion process. In effect, the extruder in the present invention functions as the rheometer itself. Unlike commercial rheometer systems for extruders, which often take several minutes between the times of sampling from main stream and determining viscosity, feedback is instant with the present system. Thus, any changes may be quickly detected and accounted for by process control. Further, the system may be used with all types of plastics, with and without fillers, unlike commercially available on-line rheometers, which may only be used on plastics without fillers. In addition; by taking in-line measurements, there is no waste generated and the need for separate capillary passages and metering pumps is averted. Finally, the in-line measured MFI, MVR and viscosity closely match results obtained in quality assurance laboratory tests.

EXPERIMENTAL

Testing was conducted on two different polymer materials on different extruder systems. The extrusion systems were previously calibrated with known polymer materials to determine values for the equation constants prior to the testing. Calculations were conducted on the measured parameters in each trial to determine MVR and viscosity, respectively. Results obtained with these measured values were compared to results obtained from using quality assurance laboratory testing techniques. The results are set forth below.

Example 1

Testing was conducted on various samples having different viscosities of a linear polycarbonate, Lexan grade, manufactured by the applicant. The extrusion process was performed on a 30 mm diameter twin screw ZSK-30 extruder obtained from Werner and Pfleiderer using a Ktron feeder. From the calibration run, the following constant values were calculated.

a=7.857×10$^{-5}$

C=−5336.2

E=−3427 n=0.3265 b=−0.137

Table 1 shows the measurements taken, with the calculated (predicted) value for MVR using equation 8 above, and the QA laboratory tested value of MVR compared.

TABLE 1

Comparison of Calculated MVR with Actual MVR

| Sample No. | Polymer Melt Temp. (° C.) | P (PSI) | Feed Rate (lb/hr) | Die Head Temp. (° C.) | MVR (QA) | MVR (predicted) |
|---|---|---|---|---|---|---|
| 1 | 314.81 | 69.17 | 59.20 | 276 | 73.1 | 75.4 |
| 2 | 310.57 | 93.44 | 78.3 | 275 | 72.2 | 72.3 |
| 3 | 329.71 | 80.55 | 33.71 | 276 | 26.4 | 28 |
| 4 | 328.03 | 147.35 | 63.04 | 274 | 27 | 24.6 |
| 5 | 339.89 | 129.65 | 30.87 | 275.5 | 11.7 | 11.7 |
| 6 | 332.82 | 195.97 | 52.66 | 275.5 | 12.5 | 12.8 |
| 7 | 322.01 | 68.60 | 69.72 | 286.5 | 72.4 | 71.5 |
| 8 | 314.91 | 98.69 | 98.55 | 286.5 | 72 | 69.6 |
| 9 | 335.18 | 88.36 | 46.08 | 287 | 26.3 | 27.6 |
| 10 | 334.60 | 114.05 | 62.64 | 287 | 25.3 | 27 |
| 11 | 352.16 | 180.18 | 35.52 | 286.5 | 6.6 | 6.4 |
| 12 | 349.41 | 210.20 | 42.99 | 287 | 6.2 | 6.6 |
| 13 | 365.63 | 230.44 | 24.39 | 283 | 2.9 | 2.7 |
| 14 | 360.97 | 279.10 | 30.6 | 284 | 2.9 | 2.8 |
| 15 | 355.56 | 104.25 | 38.14 | 301 | 12.7 | 11.8 |
| 16 | 357.79 | 150.17 | 62.98 | 301 | 12.5 | 11.7 |
| 17 | 363.01 | 141.74 | 37.38 | 304 | 6.3 | 6.7 |
| 18 | 360.97 | 192.27 | 55.43 | 305 | 6.6 | 6.7 |
| 19 | 384.12 | 174.93 | 26.20 | 306 | 2.8 | 2.6 |
| 20 | 381.711 | 255.88 | 45.6 | 307 | 2.8 | 2.8 |

Trial 2

Testing was conducted on samples of a Valox 9215Z, a 15% glass fiber filled polyethylene terephthalate (PET) resin manufactured by the applicant. The extrusion process was performed on a single screw extruder having a 6 inch diameter and a length to diameter ration (L/D) of 40 using a Ktron feeder. From the calibration run, the following constant values were calculated.

X(all)=8.439×10$^9$

C=−7894 n=−0.10644 cont.=−6.7

Table 2 shows the measurements taken, with the calculated (predicted) value for viscosity (η) using equation 10 above, and the QA laboratory tested value of η compared. The standard deviation of laboratory test for this product is 11.5 Pa.s.

TABLE 2

Comparison of Predicted Viscosity with Actual Viscosity

| Sample No. | Polymer Melt Temp. (° F.) | P (psi) | Polymer Feed Rate (lb/hr) | Viscosity (QA in Pa s) | Viscosity (Predicted in Pa.s) |
|---|---|---|---|---|---|
| 1 | 499.8 | 557.9 | 2000 | 435 | 438 |
| 2 | 493.8 | 600.5 | 2000 | 430 | 426 |
| 3 | 493.4 | 484.8 | 1600 | 432 | 438 |
| 4 | 498.6 | 454.7 | 1600 | 450 | 448 |
| 5 | 498.6 | 504 | 1800 | 443 | 437 |
| 6 | 500.4 | 600.5 | 2000 | 470 | 473 |
| 7 | 500.5 | 601 | 2000 | 475 | 474 |
| 8 | 500.3 | 601 | 2000 | 465 | 473 |
| 9 | 504.5 | 598.5 | 2000 | 505 | 503 |
| 10 | 503.7 | 580.4 | 2000 | 480 | 483 |
| 11 | 501.4 | 582.7 | 2000 | 455 | 468 |
| 12 | 503.5 | 600.1 | 2000 | 502 | 496 |
| 13 | 503.5 | 602.6 | 2000 | 505 | 498 |
| 14 | 503.3 | 525.4 | 2000 | 435 | 438 |
| 15 | 500.4 | 601.5 | 2000 | 465 | 474 |
| 16 | 501.6 | 609.9 | 2000 | 489 | 489 |
| 17 | 495.4 | 572.5 | 2000 | 424 | 419 |

The invention has been described with reference to an exemplary embodiment. Thus, the present invention has been discussed in the preceding description in conjunction with a commercial extrusion process. It should be recognized however, that the present invention is not limited to such an environment and is operable in any polymer extrusion and compounding operation in which molten polymer is discharged under pressure from a closed vessel with discharge opening having constant die geometry. Obviously, modifications and alterations will occur to others upon a reading and understanding of this specification. For instance, in case of sheet or profile extrusion for semi-crystalline plastics, this technique can be used to monitor the melting status and degradation in the process. Incomplete melting may be detected by an apparent increase in viscosity, while degradation may be detected by an apparent lowering of viscosity. The invention is intended to include all such modifications and alterations in so far as they come within the scope of the appended claims and the equivalents thereof.

What is claimed is:

1. A system for conducting in-line rheological measurements on a main process melt stream for providing process control characteristics of said polymer melt, including melt flow index (MFI), melt volume rate (MVR) and viscosity (η), said system comprising:

a vessel or extruder containing a polymer melt under pressure, a vessel head or die head connected to said vessel and defining one or more openings of any constant geometry through which said polymer melt may flow, a feeding system for providing a polymer resin to said vessel, a polymer melt temperature sensor having a portion in contact with said polymer melt in said vessel, a processing rate sensor for monitoring a rate at which a polymer resin is added to or discharged from said vessel, a vessel pressure sensor for monitoring a pressure inside said vessel, a vessel head temperature sensor for monitoring a temperature of said vessel head, and a controller responsive to signals provided by said sensors capable of substantially instantaneously determining said process characteristics of said polymer melt, said controller being adapted for calculating said control characteristics comprising said MFI, MVR and η, said controller applying a correction factor, said correction factor being selected from the group consisting of a) a melt temperature correction factor $X(T_{melt})$ wherein B and C are constants, Tmelt is the measured temperature, and $X(T_{melt})=B\ exp(C/Tmelt)$, b) a die temperature correction factor $X(T_{die})$, wherein D and E are constants, and Tdie is the measured die temperatue, and $X(T_{die})=D\ exp(E/Tdie)$, c) a shear stress correction factor $X(P)$, wherein E and n are constants, and $X(P)=E\ \Delta P^n$, and d) combinations of said correction factors.

2. A system according to claim 1, wherein said vessel comprises an extruder and said vessel head comprises a die head.

3. A system according to claim 2, further comprising one or more screws for mixing said polymer melt.

4. A system according to claim 3, wherein said polymer melt temperature sensor and said pressure sensor are located in a section in said extruder between a tip of said screw and said die head.

5. A system according to claim 1, wherein said extruder is maintained at a temperature sufficient to keep said polymer melt in a molten state.

6. A system according to claim 1, wherein said controller calculates the MFI, MVR, and η of said polymer melt using said signals and measurements obtained during a separate calibration run.

7. A system according to claim 6, wherein the difference between said calculated MFI, MVR and η and values for MFI, MVR and η obtained using quality assurance laboratory tests are within the respective standard deviation of the quality assurance laboratory measurements.

8. A system according to claim 1, wherein said orifices or die openings are of a constant geometry.

9. A system according to claim 1, wherein said polymer melt is a thermoplastic, thermoelastomer, or thermoset, with or without fillers.

10. A system according to claim 1, wherein said processing rate sensor is a feed rate sensor.

11. A system according to claim 1, wherein said processing rate sensor is a discharge rate sensor.

12. A system for providing process control characteristics concerning a polymer melt in an extrusion process, including MFI, MVR and η, the process including adding polymer resin to an extruder, forming a polymer melt from said resin, and extruding said polymer melt from a die head, said system comprising:

a processing rate sensor for monitoring a rate at which said polymer resin is added to or discharged out of the extrusion process;

a polymer melt temperature sensor for monitoring the temperature of said polymer melt prior to its extrusion;

an extrusion die pressure sensor for monitoring the pressure inside said die head;

a die head temperature sensor for monitoring the temperature of said die head; and a controller responsive to signals generated by said sensors, wherein said controller is capable of determining said process characteristics while polymer melt temperature, extrusion die pressure, and processing rate continuously vary in said extrusion process, said controller being adapted for calculating said control characteristics comprising said MFI, MVR and η, said controller applying a correction factor, said correction factor being selected from the group consisting of a) a melt temperature correction factor $X(T_{melt})$ wherein B and C are constants, Tmelt is the measured temperature, and $X(T_{melt})=B\ exp(C/Tmelt)$, b) a die temperature correction factor $X(T_{die})$, wherein D and E are constants, and Tdie is the measured die temperatue, and $X(T_{die})=D\ exp(E/Tdie)$, c) a shear stress correction factor $X(P)$, wherein E and n are constants, and $X(P)=E\ \Delta P^n$, and d) combinations of said correction factors.

13. A system according to claim 12, wherein said extrusion process is conducted in a single-screw extruder.

14. A system according to claim 12, wherein said extrusion process is conducted in a twin-screw extruder.

15. A system according to claim 12, wherein said polymer melt temperature sensor and said pressure sensor are located in a section in said extruder immediately adjacent said die head.

16. A method for providing instant process control information regarding a polymer melt in an extrusion process, including MFI, MVR and η, the method comprising the steps of:

(a) adding a polymer resin to an extruder;

(b) heating said polymer resin to form a molten polymer melt;

(c) elevating an internal pressure of said extruder to a pressure greater than atmospheric pressure;

(d) discharging said polymer melt through one or more orifices or die openings of constant geometry defined in a die head coupled to said extruder;

(e) measuring the rate at which said polymer resin is added to said extruder;

(f) measuring the temperature of said polymer melt just prior to discharge;

(g) measuring the temperature of said die head;

(h) measuring the internal pressure of said extruder;

(i) conveying said measurements to a controller; and (j) determining said process control characteristics of said polymer melt, wherein said steps (e)–(j) are performed continuously at defined intervals, and wherein said steps (i)–(j) are performed substantially simultaneously with said steps (e)–(h), (k) said measuecontroller being adapted for calculating said control characteristics and applying a correction factor to said MFI, MVR and η, said correction factor being selected from the group consisting of a) a melt temperature correction factor $X(T_{melt})$ wherein B and C are constants, Tmelt is the measured temperature, and $X(T_{melt})=B\ exp(C/Tmelt)$, b) a die temperature correction factor $X(T_{die})$, wherein D and E are constants, and Tdie is the measured die temperatue, and $X(T_{die})=D\ exp(E/Tdie)$, c) a shear stress correction factor $X(P)$, wherein E and n are constants, and $X(P)=E\ \Delta P^n$, and d) combinations of said correction factors.

17. A method according to claim 16, further comprising the step of calibrating said extruder using a polymer for which at least one of viscosity, MFI, and MVR are already known.

18. A method according to claim 17, further comprising the step of calculating viscosity, MFI and MVR for said polymer melt using said measurements and constants determined in said calibration step.

19. A method according to claim 16, wherein said step of determining said process control characteristics may be performed as measurements determined in steps (e)–(h) continuously vary during successive intervals.

20. A method according to claim 16, wherein measurements determined in steps (e)–(h) are made on a main process stream of said polymer melt.

* * * * *